(12) United States Patent
Paik (10) Patent No.: US 10,441,331 B2
(45) Date of Patent: Oct. 15, 2019

(54) FIXING TOOL FOR OPEN-WEDGE HIGH TIBIAL OSTEOTOMY

(71) Applicant: Hae Sun Paik, Seoul (KR)

(72) Inventor: Hae Sun Paik, Seoul (KR)

( * ) Notice: Subject to any disclaimer, the term of this patent is extended or adjusted under 35 U.S.C. 154(b) by 241 days.

(21) Appl. No.: 15/303,830

(22) PCT Filed: May 7, 2014

(86) PCT No.: PCT/KR2014/004036
§ 371 (c)(1),
(2) Date: Oct. 13, 2016

(87) PCT Pub. No.: WO2015/160022
PCT Pub. Date: Oct. 22, 2015

(65) Prior Publication Data
US 2017/0027627 A1 Feb. 2, 2017

(30) Foreign Application Priority Data
Apr. 18, 2014 (KR) .......................... 10-2014-0046872

(51) Int. Cl.
A61B 17/80 (2006.01)
A61B 17/82 (2006.01)
A61B 17/86 (2006.01)

(52) U.S. Cl.
CPC .......... *A61B 17/8061* (2013.01); *A61B 17/80* (2013.01); *A61B 17/8004* (2013.01);
(Continued)

(58) Field of Classification Search
CPC ...................................... A61B 17/80–17/8095
See application file for complete search history.

(56) References Cited

U.S. PATENT DOCUMENTS 6,283,969 B1 * 9/2001 Grusin ............... A61B 17/1728
606/280
7,108,697 B2 * 9/2006 Mingozzi ........... A61B 17/8095
606/286
(Continued)

FOREIGN PATENT DOCUMENTS

CN 1832706 A 9/2006
CN 102551860 A 7/2012
(Continued)

OTHER PUBLICATIONS

Extended European Search Report for EP Application No. 14889612.9 dated Nov. 27, 2017.
(Continued)

*Primary Examiner* — Zade Coley
(74) *Attorney, Agent, or Firm* — STIP Law Group, LLC (57) ABSTRACT

The present invention relates to a fixing tool for an open-wedge high tibial osteotomy, and the fixing tool for an open-wedge high tibial osteotomy, which is installed on a tibia cut open due to an open-wedge tibial osteotomy, includes: a fixing plate which includes a head portion that has a plurality of head nut holes, and an elongated plate that has an upper nut hole, a lower nut hole, and a long hole formed between the upper nut hole and the lower nut hole, and protrudes from one side of the head portion; screws which are coupled to the head nut holes, the upper nut hole, and the lower nut hole so as to fix the fixing plate to the tibia; and a support screw which is installed by being moved along the long hole formed to be spaced apart at a predetermined interval from the upper nut hole formed at a side adjacent to the head portion. Therefore, the fixing tool is closely fixed to a tibia, which has been cut open due to a procedure of a high tibial osteotomy, thereby enabling solid union of the tibia.

12 Claims, 7 Drawing Sheets

(52) U.S. Cl.
CPC .......... *A61B 17/8095* (2013.01); *A61B 17/82* (2013.01); *A61B 17/86* (2013.01)

(56) References Cited

U.S. PATENT DOCUMENTS

| | | | | |
|---|---|---|---|---|
| 7,635,381 | B2* | 12/2009 | Orbay | A61B 17/8057 606/291 |
| 7,951,176 | B2* | 5/2011 | Grady, Jr. | A61B 17/746 606/280 |
| 8,182,517 | B2* | 5/2012 | Sixto, Jr. | A61B 17/8061 606/280 |
| 8,246,660 | B2* | 8/2012 | Boris | A61B 17/808 606/246 |
| 2002/0156474 | A1* | 10/2002 | Wack | A61B 17/1728 606/281 |
| 2003/0199875 | A1* | 10/2003 | Mingozzi | A61B 17/8095 606/297 |
| 2004/0172028 | A1* | 9/2004 | Roger | A61B 17/8095 606/71 |
| 2005/0015089 | A1* | 1/2005 | Young | A61B 17/8014 606/915 |
| 2005/0245931 | A1* | 11/2005 | Orbay | A61B 17/1728 606/291 |
| 2005/0251138 | A1* | 11/2005 | Boris | A61B 17/7071 623/17.11 |
| 2006/0004362 | A1* | 1/2006 | Patterson | A61B 17/8057 606/291 |
| 2006/0173458 | A1* | 8/2006 | Forstein | A61B 17/1728 606/86 B |
| 2008/0015593 | A1* | 1/2008 | Pfefferle | A61B 17/8052 606/282 |
| 2009/0177203 | A1* | 7/2009 | Reiley | A61B 17/8095 606/87 |
| 2010/0016858 | A1* | 1/2010 | Michel | A61B 17/8057 606/70 |
| 2010/0241173 | A1* | 9/2010 | Orbay | A61B 17/8057 606/286 |
| 2012/0184959 | A1* | 7/2012 | Price | A61B 17/8009 606/70 |
| 2013/0138154 | A1* | 5/2013 | Reiley | A61B 17/8095 606/280 |
| 2013/0245699 | A1 | 9/2013 | Orbay et al. | |
| 2013/0296943 | A1 | 11/2013 | Grady, Jr. et al. | |

FOREIGN PATENT DOCUMENTS

| | | |
|---|---|---|
| EP | 1 308 135 A2 | 5/2003 |
| EP | 2 510 893 A1 | 10/2012 |
| JP | 2006-312062 A | 11/2006 |
| JP | 2007-151674 A | 6/2007 |
| JP | 2009-502336 A | 1/2009 |
| JP | 2009-247681 A | 10/2009 |
| JP | 2010-220762 A | 10/2010 |
| JP | 2011-505199 A | 2/2011 |
| KR | 10-2006-0035604 A | 4/2006 |
| KR | 10-0884491 B1 | 2/2009 |
| KR | 10-1253915 B1 | 4/2013 |
| KR | 10-1342493 B1 | 12/2013 |
| WO | WO 01/56452 A2 | 8/2001 |
| WO | WO 2007/100513 A2 | 9/2007 |

OTHER PUBLICATIONS

International Search Report for International Patent Application No. PCT/KR2014/004036 filed May 7, 2014.

* cited by examiner

FIXING TOOL FOR OPEN-WEDGE HIGH TIBIAL OSTEOTOMY

CROSS REFERENCE TO RELATED APPLICATIONS

The present application is a U.S. National Stage of International Patent Application No. PCT/KR2014/004036 filed May 7, 2014, which claims priority to and the benefit of Korean Patent Application No. 10-2014-0046872 filed in the Korean Intellectual Property Office on Apr. 18, 2014, the entire contents of which are incorporated herein by reference.

TECHNICAL FIELD

The present invention relates to a fixing tool for an open-wedge high tibial osteotomy. More particularly, the present invention relates to a fixing tool for an open-wedge high tibial osteotomy, which is fixed to a tibia, which has been cut open after an interior high tibial osteotomy, so as to enable solid union of the tibia.

BACKGROUND ART

Osteoarthritis causes angular deformity, which results from severe breakdown of joint cartilage of an inner knee joint, and results in pain, and when a patient stands or walks, progression of arthritis and pain become more severe because a body weight is concentrated to one side.

For performing a procedure for inward angular deformity, a method is used which performs an osteotomy on an inner proximal tibia in the vicinity of a knee, and then fixes the tibia by using a metallic plate.

The high tibial osteotomy is a method of performing an osteotomy on a proximal portion of the tibia so as to reduce pain by dispersing a load of body weight, which is concentrated to an interior of a knee joint, further outward.

Figure 1:
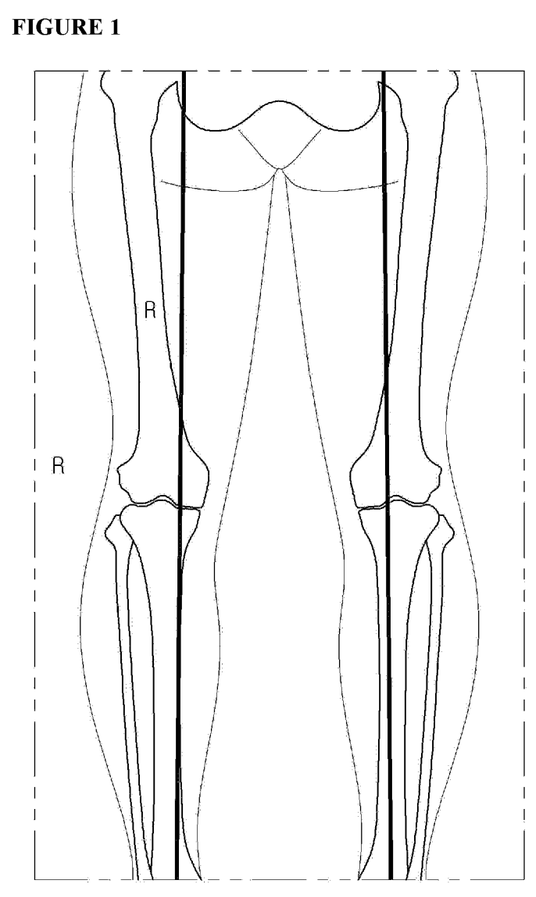
FIG. 1 is an X-ray photograph of a person required to be subjected to a procedure of a high tibial osteotomy.

As illustrated in FIG. 1, assuming that a line, which connects a center of a coxa and a center of an ankle, is an axis of a lower limb, the line means a weight-bearing line while walking, and in a normal situation, the line runs through a center of the knee.

Therefore, the high tibial osteotomy refers to a procedure that allows the line to run through the center of the knee. Therefore, after the procedure, comparatively normal articulation motions, such as squatting and running, are enabled.

As the invention associated with the high tibial osteotomy, there is Korean Patent No. 10-1253915 (Apr. 5, 2013) "Connector for High Tibia Osteotomy".

Figure 2:
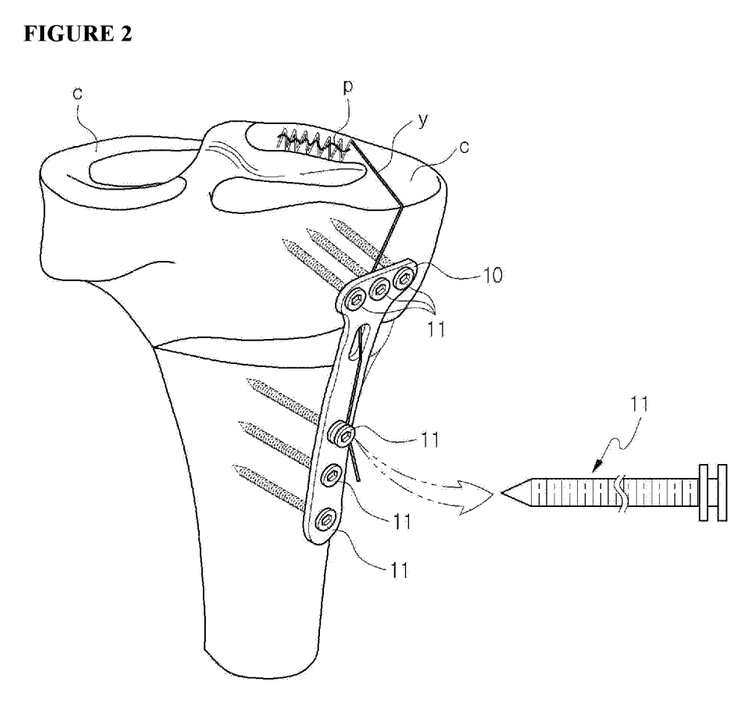
FIG. 2 is a view illustrating a connector for a high tibial osteotomy in the related art.

Referring to FIG. 2, the connector for a high tibia osteotomy is characterized in that a through hole, through which a medical grade suture remaining after sewing a wound of a cartilage may pass, is formed in the form of a long hole.

However, because a main connecting body 10 of the disclosed connector for a high tibial osteotomy is formed in the form of a flat plate, there is a problem in that close contact force with an outer surface of the tibia deteriorates during a procedure of the high tibial osteotomy.

In addition, when fixing the main connecting body 10, screws 11 need to be coupled by using a separate tool to fix the main connecting body 10 or a practitioner needs to hold the main connecting body 10 to couple the screws 11, and as a result, there is difficulty in selecting a position of the main connecting body 10 and fixing the main connecting body 10.

Therefore, there is a problem in that a period of time required for the procedure is prolonged.

SUMMARY OF THE INVENTION

Technical Problem

Accordingly, the present invention has been made in an effort to solve the aforementioned problems, and an object of the present invention is to provide a fixing tool for an open-wedge high tibial osteotomy, which is fixed to a tibia, which has been cut open after an interior high tibial osteotomy, so as to enable solid union of the tibia.

In addition, another object of the present invention is to provide a fixing tool for an open-wedge high tibial osteotomy, which is closely fixed to the tibia, which has been cut open due to an open-wedge high tibial osteotomy, so as to facilitate a procedure and union of the tibia and support a load applied to the tibia.

Technical Solution

According to the present invention, the aforementioned object is achieved by a fixing tool for an open-wedge high tibial osteotomy, which is installed on a tibia cut open due to an open-wedge tibial osteotomy, the fixing tool including: a fixing plate which includes a head portion that has a plurality of head nut holes, and an elongated plate that has an upper nut hole, a lower nut hole, and a long hole formed between the upper nut hole and the lower nut hole, and protrudes from one side of the head portion; screws which are coupled to the head nut holes, the upper nut hole, and the lower nut hole so as to fix the fixing plate to the tibia; and a support screw which is installed by being moved along the long hole formed to be spaced apart at a predetermined interval from the upper nut hole formed at a side adjacent to the head portion.

Here, the head portion may be curvedly formed at a predetermined curvature.

Further, as the head portion is curvedly formed, the screws, which are installed in the nut holes formed at both sides of the head nut hole formed at a center of the head portion, may be installed to be inclined toward a center of the curvature.

In addition, tips of the screws, which are installed toward a centerline, that connects a center of the head portion and a center of the curvature, and installed at both sides based on the center of the head portion, may be installed to be spaced apart from the centerline.

In addition, the nut hole formed in the head portion may be inclinedly formed to have a gradient of 8 to 12 degrees in a direction toward the elongated plate.

In addition, the other side of the head portion may be inclinedly formed to have an inclination angle.

Here, the inclination angle may be 5 to 7 degrees.

In addition, a portion of the elongated plate connected with the head portion may be bent to have a bending angle.

Here, the bending angle may be 13 to 16 degrees.

In addition, a width of the elongated plate may be curvedly formed at a predetermined curvature.

In addition, the plurality of lower nut holes may be disposed to be zigzag from each other in a longitudinal direction of the elongated plate.

Meanwhile, the screw installed in the upper nut hole may be installed to be inclined toward the head portion.

Further, a length of the screw installed in the upper nut hole may be smaller than that of the screw installed in the head portion.

In addition, the fixing plate may have at least three guide holes formed such that guide pins are installed in at least three guide holes.

That is, the head portion may have two guide holes, the elongated plate may have one guide hole, and the guide hole formed in the elongated plate may be formed at a side adjacent to a patella.

In addition, the predetermined interval may be 17 to 21 mm.

Advantageous Effects

The fixing tool for an open-wedge high tibial osteotomy according to the exemplary embodiment of the present invention, which has the aforementioned configuration, is closely fixed to the tibia which has been cut open due to the high tibial osteotomy, thereby enabling solid union of the tibia.

That is, the fixing plate is curvedly formed at a predetermined curvature, and a portion of the fixing plate is bent and then closely attached to the tibia, thereby improving integrality with the tibia.

In addition, since the fixing tool for an open-wedge high tibial osteotomy is temporarily fixed by using a guide pin, it is possible to ensure convenience of a procedure of the open-wedge high tibial osteotomy.

DETAILED DESCRIPTION

Hereinafter, exemplary embodiments of the present invention will be described in detail with reference to the accompanying drawings in order to clarify solutions for solving the technical problems of the present invention. However, in the description of the present invention, a detailed explanation of publicly known related technologies will be omitted in order to avoid unnecessarily obscuring the subject matter of the present invention. In addition, the following terms are defined considering the functions of the present invention and may vary depending on the intention or usual practice of a designer or a manufacturer. Therefore, the definitions thereof should be made based on the entire contents of the present specification. In addition, like drawing numerals (reference numerals) indicate like elements throughout the specification.

Hereinafter, a fixing tool for an open-wedge high tibial osteotomy according to an exemplary embodiment of the present invention will be described.

Figure 3:
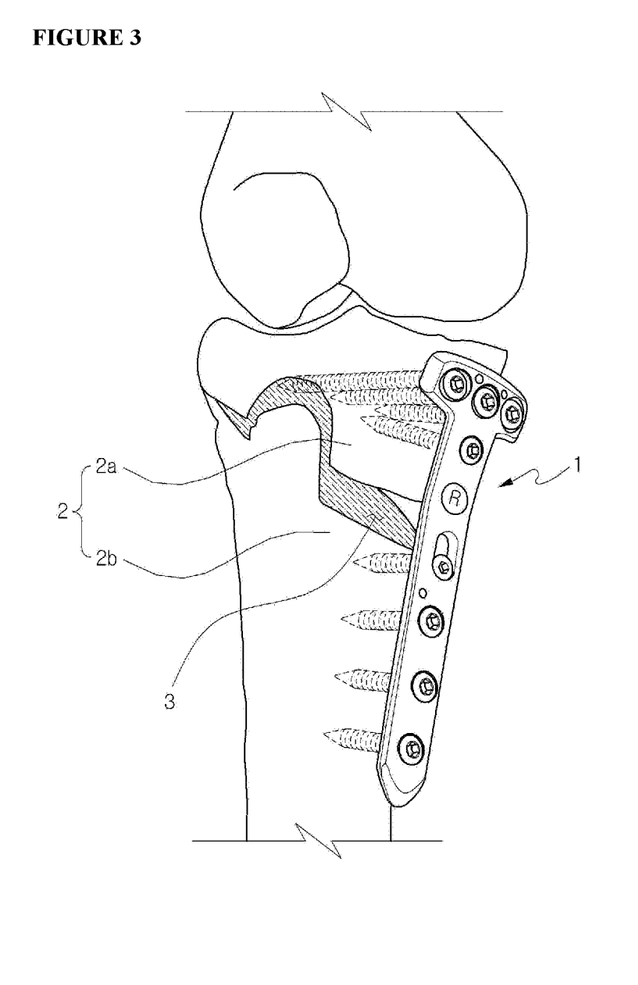
FIG. 3 is a view illustrating a state in which a fixing tool for an open-wedge high tibial osteotomy according to an exemplary embodiment of the present invention is used.

Referring to FIG. 3, a cut-out portion 3 is formed due to a procedure of an open-wedge high tibial osteotomy that cuts a tibia 2. Therefore, the tibia 2 is divided into an upper tibia 2a and a lower tibia 2b.

A fixing tool 1 for an open-wedge high tibial osteotomy according to an exemplary embodiment of the present invention is closely fixed to the upper tibia 2a and the lower tibia 2b, which have been cut open due to the tibial osteotomy, thereby facilitating union of the upper tibia 2a and the lower tibia 2b after the procedure.

In addition, the fixing tool 1 for an open-wedge high tibial osteotomy supports a load applied to the tibia 2 until the union of the upper tibia 2a and the lower tibia 2b.

Referring to FIGS. 4 to 7, the fixing tool 1 for an open-wedge high tibial osteotomy may include a fixing plate 100, screws 200, and a support screw 300.

Figure 5:
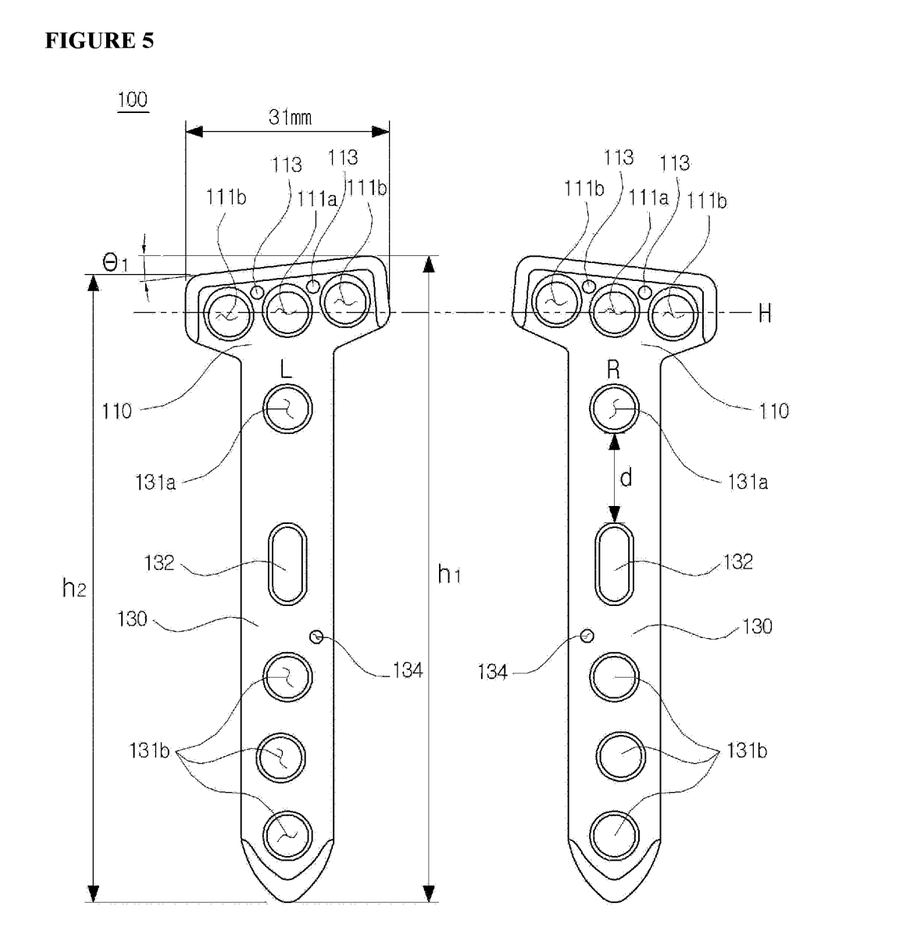
FIG. 5 is a view illustrating left and right fixing plates of the fixing tool for an open-wedge high tibial osteotomy according to the exemplary embodiment of the present invention.

As illustrated in FIG. 5, the fixing plate 100 may be classified into a left fixing plate L and a right fixing plate R, and the left fixing plate L and the right fixing plate R may be selectively used depending on the tibia 2 to be subjected to the procedure.

The fixing plate 100 may include a head portion 110 and an elongated plate 130.

The elongated plate 130 is formed to protrude from one side of the head portion 110, and thus the fixing plate 100 may be formed in a T shape as illustrated in FIG. 5.

Here, a thickness of the fixing plate 100 is about 3 mm, and an overall length of the fixing plate 100 is 100 to 103 mm, and a length of the head portion 110 in a longitudinal direction may be 31 mm.

A plurality of nut holes 111a, 111b, 131a, and 131b is formed in the head portion 110 and the elongated plate 130, respectively, so that the screws 200 may be coupled to the plurality of nut holes 111a, 111b, 131a, and 131b. To clearly describe the present invention, the plurality of nut holes 111a, 111b, 131a, and 131b may be classified into the head nut holes 111a and 111b formed in the head portion 110, and the nut holes 131a and 131b formed in the elongated plate 130. In addition, the nut holes 131a and 131b formed in the elongated plate 130 may be classified into the upper nut hole 131a and the lower nut hole 131b based on the positions where the nut holes 131a and 131b are formed.

Here, the nut holes 111a, 111b, 131a, and 131b each are formed to have a wide upper side and a narrow lower side by being cut away to have a tapered shape. Therefore, heads of the screws 200 are matched in shape with the nut holes 111a, 111b, 131a, and 131b. Further, the heads of the screws 200 are supported by the nut holes 111a, 111b, 131a, and 131b.

Figure 6:
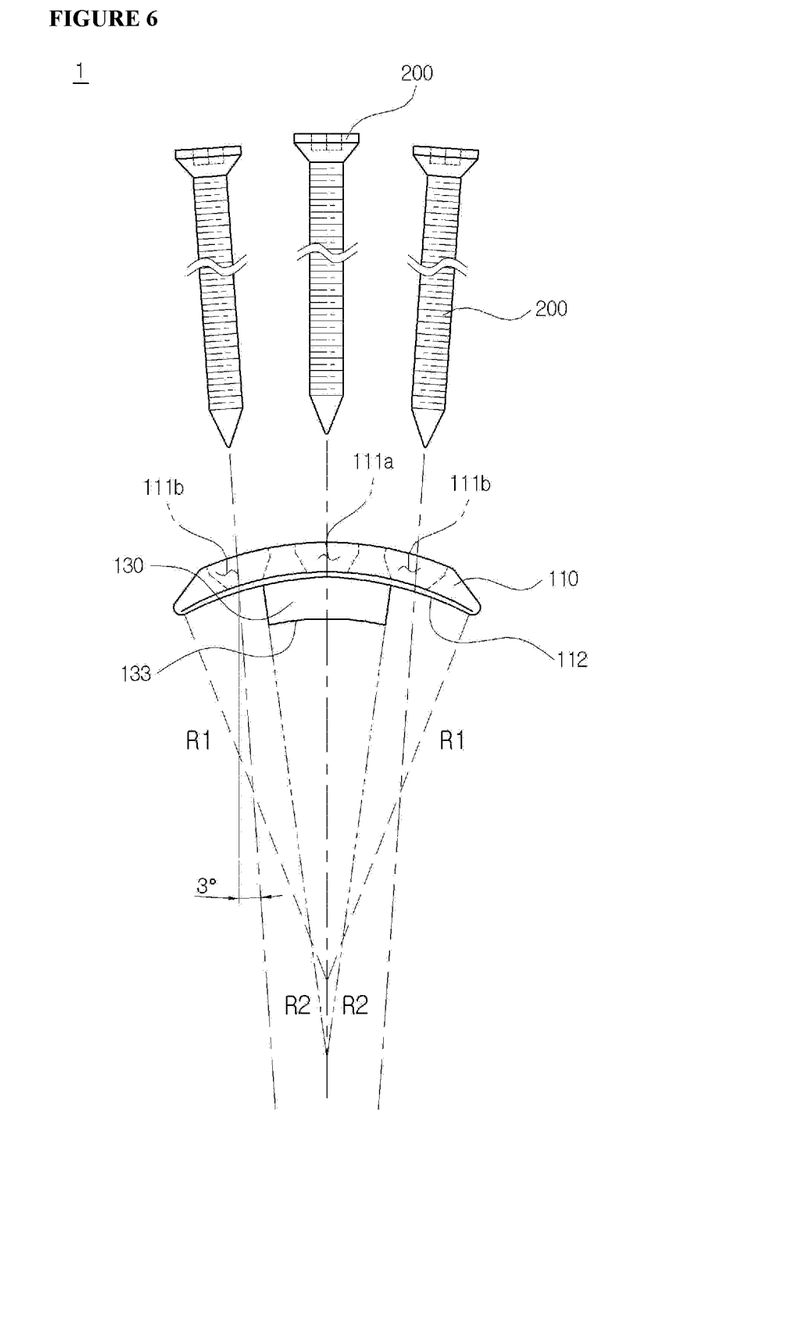
FIG. 6 is a view illustrating a head portion and a radius of curvature of an elongated plate of the fixing tool for an open-wedge high tibial osteotomy according to the exemplary embodiment of the present invention.

Referring to FIG. 6, the head portion 110 are curvedly formed to have a predetermined radius of curvature R1. In particular, a head close contact surface 112 of the head portion 110 is curvedly formed to have the predetermined radius of curvature R1 so that the head close contact surface 112 may be closely attached to one side of an outer surface of the upper tibia 2a.

Further, since the head close contact surface 112 of the head portion 110 is curvedly formed, the screw 200 installed in the head nut hole 111b may be installed to be inclined toward a center of the radius of curvature R1 as illustrated in FIG. 6.

Of course, the screw 200 installed in the head nut hole 111b may be installed to be inclined toward the center of the radius of curvature R1 as described above, but the present invention is not necessarily limited thereto, and an angle at which the screw 200 installed in the head nut hole 111b is installed may be adjusted by adjusting an angle at which the head nut hole 111b is formed.

Therefore, as illustrated in FIG. 6, in consideration of a separation interval between the screw 200 installed in the head nut hole 111a and the screw 200 installed in the head nut hole 111b, the screw 200 installed in the head nut hole 111b may be installed to be inclined at about 2 to 4 degrees based on a central axis in the longitudinal direction of the screw 200 installed in the head nut hole 111a, and may be installed to be inclined at about 3 degrees.

That is, the screw 200 installed in the head nut hole 111b is installed toward a centerline that connects a center of the head portion 110 and the center of the radius of curvature R1, and a tip of the screw 200 installed in the head nut hole 111b is installed to be spaced apart from the centerline.

Figure 7:
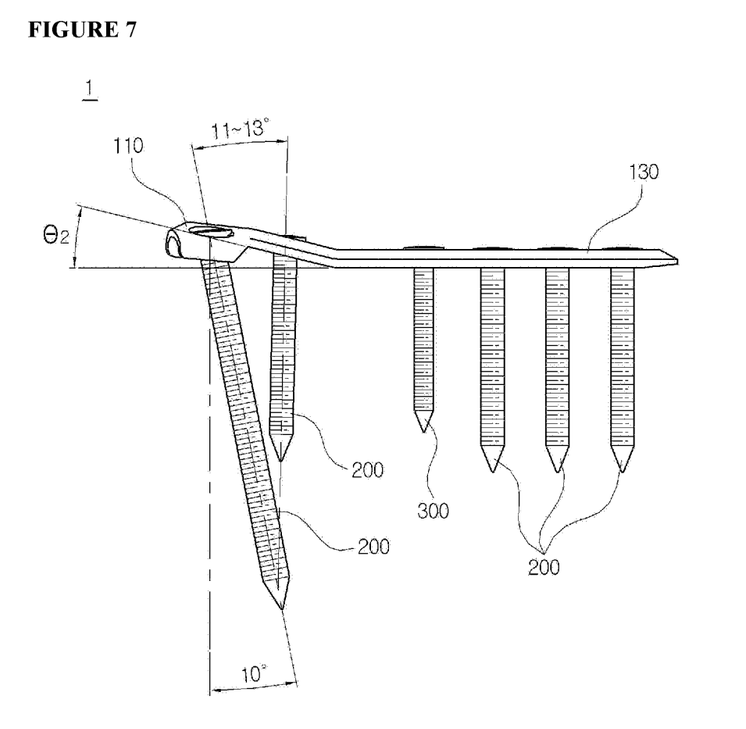
FIG. 7 is a side view of the fixing tool for an open-wedge high tibial osteotomy according to the exemplary embodiment of the present invention.

Meanwhile, as illustrated in FIG. 7, the head nut holes 111a and 111b formed in the head portion 110 may be formed to have a gradient of 8 to 12 degrees in a direction toward the elongated plate 130. In particular, the head nut holes 111a and 111b may be formed to have a gradient of 10 degrees.

Therefore, the screws 200 installed in the head nut holes 111a and 111b formed in the head portion 110 are installed in the upper tibia 2a with a gradient of 10 degrees in the direction toward the elongated plate 130. Therefore, the plurality of screws 200 installed in the upper tibia 2a may easily cope with a load applied to the fixing tool 1 for an open-wedge high tibial osteotomy.

In addition, since the screws 200 installed in the head nut holes 111a and 111b are fixedly installed in the upper tibia 2a with a gradient of 10 degrees in the direction toward the elongated plate 130, the screws 200 are not easily withdrawn from the upper tibia 2a by external force and the load.

As illustrated in FIG. 5, the head portion 110 may be inclinedly formed to have an inclination angle θ1 based on an imaginary horizontal line H that transverses the center of the head portion 110. That is, an edge of the head portion 110, which is opposite to a portion connected to the elongated plate 130, may be inclinedly formed to have the inclination angle θ1.

Here, the inclination angle θ1 may be 5 to 7 degrees.

Therefore, a height h1 from an end of the elongated plate 130 to one side of a side edge of the head portion 110 is greater than a height h2 of the other side of the head portion 110.

Since the height h1 of one side of the side edge is greater than the height h2 of the other side, a contact area between the tibia 2 and the side edge h1 of the fixing tool 1 for an open-wedge high tibial osteotomy is increased. Therefore, the procedure is carried out such that the side edge h1 is positioned at a front side (a patella side) of the tibia 2, and as a result, it is possible to more easily cope with a load applied to the front side of the tibia 2. In addition, it is also possible to easily cope with external force applied from the front side of the tibia 2.

The head portion 110 may further include at least two guide holes 113 formed such that guide pins (not illustrated) are installed in at least two guide holes 113.

The guide pins are installed in the upper tibia 2a while penetrating the guide holes 113 before the screws 200 are installed, and as a result, the head portion 110 of the fixing plate 100 is temporarily fixed.

Therefore, the guide pin prevents the fixing plate 100 from being moved linearly when the screws 200 are installed in the fixing plate 100. In addition, it is not necessary for a practitioner to hold the fixing plate 100 in order to install the screws 200.

Hereinafter, the elongated plate 130 will be described with reference to FIGS. 5 to 7.

As illustrated in FIG. 6, the elongated plate 130 may be curvedly formed in a width direction.

The elongated plate 130 is curvedly formed to have a predetermined radius of curvature R2. In particular, a plate close contact surface 133 of the elongated plate 130 is curvedly formed to have the predetermined radius of curvature R2 so that the plate close contact surface 133 may be closely attached to one side of an outer surface of the lower tibia 2b.

The radius of curvature R2 of the plate close contact surface 133 may be different from the radius of curvature R1 of the head close contact surface 112. In particular, the radius of curvature R2 of the plate close contact surface 133 may be greater than the radius of curvature R1 of the head close contact surface 112.

That is, because the outer surface of the lower tibia 2b may be formed as a flat outer surface unlike the upper tibia 2a, the radius of curvature R2 of the plate close contact surface 133 may be greater than the radius of curvature R1 of the head close contact surface 112 in accordance with a position of the tibia 2 to be subjected to the tibial osteotomy.

Referring to FIG. 7, a portion of the elongated plate 130 connected with the head portion 110 may be bent to have a bending angle θ2. Here, the bending angle θ2 may be 13 to 16 degrees, and particularly, 15 degrees.

Because an outer diameter of the upper tibia 2a is greater than an outer diameter of the lower tibia 2b, the elongated plate 130, which is bent from the head portion 110 with the bending angle θ2, is easily closely attached to the lower tibia 2b.

Meanwhile, the elongated plate 130 protrudes from one side of the head portion 110, and may have the upper nut hole 131a, the lower nut holes 131b, and along hole 132.

Figure 4:
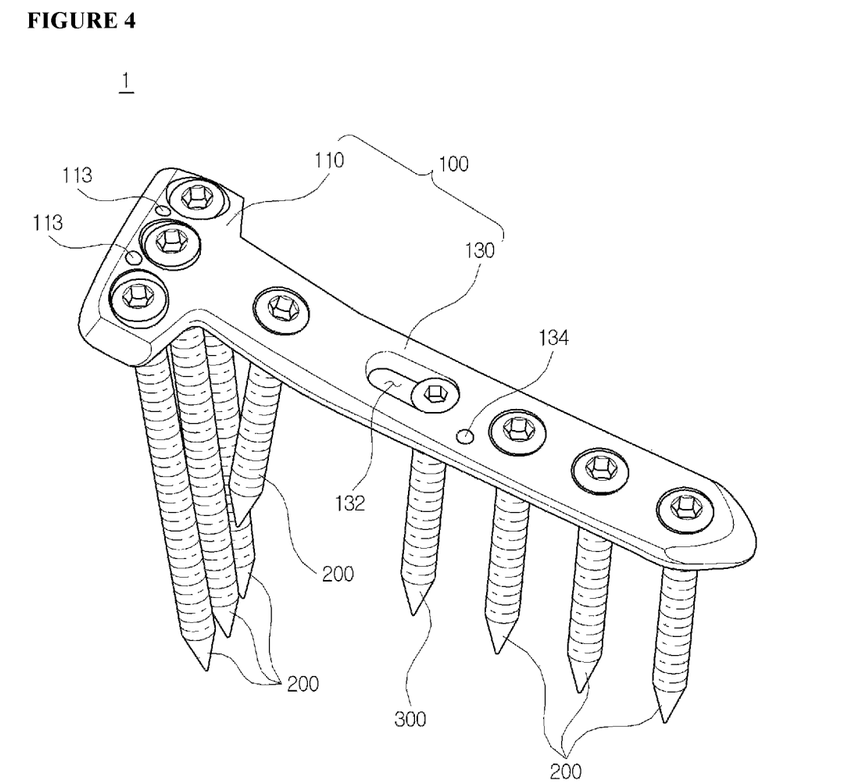
FIG. 4 is a perspective view illustrating the fixing tool for an open-wedge high tibial osteotomy according to the exemplary embodiment of the present invention.

As illustrated in FIGS. 4 and 5, the upper nut hole 131a may be formed in the elongated plate 130 at a side adjacent to the head portion 110. Further, the screw 200 is penetratively installed in the upper nut hole 131a. Here, the screw 200 installed in the upper nut hole 131a may be fixedly installed in the upper tibia 2a so as to be inclined toward the head portion 110.

As illustrated in FIG. 7, an angle between the screw 200 installed in the upper nut hole 131a and the screw 200 installed in the head nut hole 111a or 111b may be 11 to 13 degrees.

Therefore, the screw 200 installed in the upper nut hole 131a is prevented from being exposed to the cut-out portion 3.

In addition, a length of the screw 200 installed in the upper nut hole 131a is smaller than a length of the screw 200 installed in the head portion 110. Therefore, when the screws 200 are installed, the screw 200 installed in the upper nut hole 131a and the screw 200 installed in the head portion 110 do not interfere with each other.

The long hole 132 formed between the upper nut hole 131a and the lower nut hole 131b is elongated in the longitudinal direction of the elongated plate 130.

Further, the long hole 132 may be formed to be spaced apart from the upper nut hole 131a at a predetermined interval d. Here, the predetermined interval d may be 17 to 21 mm in consideration of a gap in the cut-out portion 3, and may be 21 mm in consideration of a support function of the support screw 300 installed in the long hole 132 and a likelihood of a fracture of the lower tibia 2b caused by the support screw 300.

The support screw 300 may be installed in the long hole 132.

Therefore, the support screw 300 is moved along the long hole 132, and then fixedly installed in the lower tibia 2b.

Meanwhile, as illustrated in FIGS. 4 and 5, the plurality of lower nut holes 131b may be formed in the elongated plate 130. Further, since the screws 200 are installed in the lower nut holes 131b, the elongated plate 130 is installed to be closely attached to the lower tibia 2b.

Here, the plurality of lower nut holes 131b may be disposed to be zigzag from each other in the longitudinal direction of the elongated plate 130.

Therefore, the screws 200, which are installed to be zigzag from each other in the lower nut holes 131b, disperse a load, which is applied along the central axis in the longitudinal direction of the elongated plate 130, in the width direction.

In addition, in comparison with lower nut holes 131b formed along the central axis in the longitudinal direction of the elongated plate 130, a separation distance between the lower nut holes 131b installed to be zigzag from each other is greater than a separation distance between the lower nut holes 131b formed along the central axis in the longitudinal direction of the elongated plate 130.

Therefore, distances between the screws 200 installed in the lower nut holes 131b are also increased. That is, since a separation distance between the screws 200 installed in the lower nut holes 131b is increased, a likelihood of a fracture of the lower tibia 2b is reduced.

Meanwhile, a guide hole 134 may be further formed in the elongated plate 130.

The guide pin (not illustrated) is installed in the guide hole 134, and temporarily fixes the elongated plate 130 to the lower tibia 2b.

Therefore, as illustrated in FIGS. 4 and 5, the fixing plate 100 has the two guide holes 113 in the head portion 110 and the single guide hole 134 in the elongated plate 130.

In particular, the guide hole 134 to be formed in the elongated plate 130 may be formed at a side adjacent to the patella. Because a person to be subjected to the open-wedge high tibial osteotomy lies during the procedure, the guide pin may be easily installed by forming the guide hole 134 in the elongated plate 130 at the side adjacent to the patella.

As described above, the fixing plate 100 has at least three guide holes 113 and 134.

Therefore, since the fixing plate 100 is temporarily fixed at three points, it is possible to prevent the fixing plate 100 from being moved in a rotational direction as well as a linear direction. Further, the screws 200 are installed in the fixing plate 100 in order to closely fix the fixing plate 100 to the tibia 2. Then, the guide pins are removed.

Collectively, the fixing tool 1 for an open-wedge high tibial osteotomy is closely fixed to the tibia 2, which has been cut open due to the high tibial osteotomy, and supports a load applied to the tibia 2, thereby allowing bone growth into the cut-out portion 3 and enabling a quick union.

The various exemplary embodiments according to the present invention may of course solve a variety of technical problems other than the contents mentioned in the present specification in the related technical field as well as the corresponding technical field.

As the foregoing, the present invention has been described with reference to the exemplary embodiments. However, those skilled in the art will clearly understand that the present invention may be embodied in any other modified form without departing from the basic technical spirit of the present invention. Thus, it should be appreciated that the disclosed exemplary embodiments are intended to be illustrative, not restrictive. That is, it should be construed that the true technical scope of the present invention is determined by the appended claims, and all differences within the equivalent scope thereto are included in the scope of the present invention.

The invention claimed is:

1. A fixing tool for an open-wedge high tibial osteotomy, which is configured to be installed on a tibia cut open due to an open-wedge tibial osteotomy, the fixing tool comprising:
    a fixing plate comprising:
        a head portion with an upper side, a lower side opposite to the upper side, a left side directly contacting the upper side at a left edge, a right side directly contacting the upper side at a right edge, a top surface, and a bottom surface, the head portion comprising a plurality of head nut holes that penetrate the top surface and the bottom surface, and
        an elongated plate portion protruding from the lower side of the head portion in a longitudinal direction that is perpendicular to a width direction, the elongated plate portion comprising an upper nut hole, a lower nut hole, and an elongated hole formed between the upper nut hole and the lower nut hole and spaced apart from the upper nut hole at a predetermined interval;
    screws which are coupled to the head nut holes, the upper nut hole, and the lower nut hole configured to fix the fixing plate to the tibia; and
    a support screw which is installed in the elongated hole, wherein the head portion has a predetermined curvature with a first radius, and the head nut holes include at least two nut holes that are canted with respect to the curvature, the elongated plate portion has a predetermined curvature with a second radius in the width direction, and the second radius is greater than the first radius,
    wherein a first center of a circle defined by the first radius is offset from a second center of a circle defined by the second radius, and
    wherein the upper side is inclined from the width direction at an inclination angle.

2. The fixing tool of claim 1, wherein the head nut holes are inclined to have a gradient of 8 to 12 degrees in a direction toward the elongated plate portion.

3. The fixing tool of claim 1, wherein the inclination angle is 5 to 7 degrees.

4. The fixing tool of claim 1, wherein a portion of the elongated plate portion connected with the head portion is bent to have a bending angle.

5. The fixing tool of claim 4, wherein the bending angle is 13 to 16 degrees.

6. The fixing tool of claim 1, wherein a plurality of the lower nut holes are disposed to be zigzag from each other in a longitudinal direction of the elongated plate portion.

7. The fixing tool of claim 1, wherein the screw installed in the upper nut hole is installed to be inclined toward the head portion.

8. The fixing tool of claim 7, wherein a length of the screw installed in the upper nut hole is smaller than that of the screw installed in the head portion.

9. The fixing tool of claim 1, wherein the fixing plate includes at least three guide holes formed such that guide pins are installed in at least three guide holes.

10. The fixing tool of claim 9, wherein the head portion has two guide holes, the elongated plate has one guide hole, and the guide hole formed in the elongated plate portion is formed at a side configured to be placed adjacent to a patella.

11. The fixing tool of claim 1, wherein the predetermined interval is 17 to 21 mm.

12. The fixing tool of claim 1, wherein the head nut holes are inclined to have a gradient of 8 to 12 degrees in a direction toward the elongated plate portion, wherein the inclination angle is 5 to 7 degrees, wherein a portion of the elongated plate portion connected with the head portion is bent to have a bending angle of 13 to 16 degrees, and wherein the predetermined interval is 17 to 21 mm.

* * * * *